US00PP22178P2

(12) United States Plant Patent
Bergman

(10) Patent No.: US PP22,178 P2
(45) Date of Patent: Oct. 4, 2011

(54) ***CHRYSANTHEMUM* PLANT NAMED 'YOGRAND RAPIDS'**

(50) Latin Name: *Chrysanthemum×morifolium*
Varietal Denomination: Yograng Rapids

(75) Inventor: Wendy R. Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 158 days.

(21) Appl. No.: 12/653,684

(22) Filed: Dec. 17, 2009

(51) Int. Cl.
*A01H 5/00* (2006.01)

(52) U.S. Cl. ..... Plt./289

(58) Field of Classification Search ..... Plt./287, Plt./289
See application file for complete search history.

(56) References Cited

U.S. PATENT DOCUMENTS

| | | | | |
|---|---|---|---|---|
| PP10,800 | P * | 2/1999 | Wain | Plt./289 |
| PP11,896 | P2 * | 5/2001 | Boeder | Plt./289 |
| PP17,438 | P2 * | 2/2007 | Bergman | Plt./287 |
| PP18,905 | P2 * | 6/2008 | Lintott | Plt./289 |

OTHER PUBLICATIONS

UPOV ROM GTITM Computer Database, GTI Jouve Retrieval Software 2011/01 "CA" Citation for 'Yograng Rapids'.*
UPOV ROM GTITM Computer Database, GTI Jouve Retrieval Software 2011/01 "BR" Citation for 'Yograng Rapids'.*

* cited by examiner

*Primary Examiner* — Wendy C Haas
(74) *Attorney, Agent, or Firm* — S. Matthew Edwards

(57) ABSTRACT

A new *Chrysanthemum* plant named 'Yograng Rapids' particularly distinguished by the light yellow ray florets with a greyed-red center, decorative type, fully double flower, medium green foliage, fast flowering response time, good stem strength, and excellent shelf-life.

1 Drawing Sheet

Latin name of the genus and species of the plant claimed: *Chrysanthemum×morifolium.*
Varietal denomination: 'Yograng Rapids'.

BACKGROUND OF THE NEW PLANT

The present invention comprises a new *Chrysanthemum*, botanically known as *Chrysanthemum×morifolium*, and hereinafter referred to by the variety name 'Yograng Rapids.'

'Yograng Rapids' is a product of a planned breeding program. The new cultivar has light yellow ray florets with a greyed-red center, decorative type, fully double flower, medium green foliage, fast flowering response time, good stem strength, and excellent shelf-life.

'Yograng Rapids' originated from a hybridization made in May 2005 in a controlled breeding environment in Salinas, Calif. The female parent was the proprietary, unpatented plant designated 'YB-A9207' with bronze two tone flower color, a 9 week flowering response time, and has a taller growing plant habit.

The male parent of 'Yograng Rapids' was an proprietary, unpatented plant identified as 'YB-A8021' with red decorative, open centered flowers, an 8 week flowering response time, less vigor, and moderate pollen production.

'Yograng Rapids' was selected as one flowering plant within the progeny of the stated cross in December 2005, grown out doors in a field covered by saran in Fort Myers, Fla.

The first act of asexual reproduction of 'Yograng Rapids' was accomplished when vegetative cuttings were propagated from the initial selection in March 2006 in a controlled environment in Fort Myers, Fla.

BRIEF SUMMARY OF INVENTION

Horticultural examination of plants grown from cuttings of the plant initiated in March 2006, and continuing thereafter, has demonstrated that the combination of characteristics as herein disclosed for 'Yograng Rapids' are firmly fixed and are retained through successive generations of asexual reproduction.

'Yograng Rapids' has not been observed under all possible environmental conditions. The phenotype may vary significantly with variations in environment such as temperature, light intensity and day length.

A Plant Breeder's Right for this cultivar was applied for in Canada on Mar. 24, 2009. 'Yograng Rapids' has not been made publicly available more than one year prior to the filing of this application.

The following traits have been repeatedly observed and are determined to be basic characteristics of the new variety. The combination of these characteristics distinguishes this *Chrysanthemum* as a new and distinct variety

BRIEF DESCRIPTION OF THE PHOTOGRAPHS

The accompanying photographic drawing shows typical flower and foliage characteristics of 'Yograng Rapids' with colors being as true as possible with an illustration of this type. The photographic drawing shows four flowering potted plants of the new variety growing in a five inch pot, and a close-up of the flowers.

DETAILED BOTANICAL DESCRIPTION

The plant descriptions, measurements and aforementioned photographs were taken in Gilroy, Calif. in April 2009 under greenhouse conditions. These plants were started and grown in central coastal California, then shipped to Gilroy, Calif. in April 2009. Plants were grown under conditions which approximate those generally used in commercial potted *Chrysanthemum* production and were about 10 weeks of age.

Color references are made to The Royal Horticultural Society Colour Chart (R.H.S.) 2001.

TABLE 1

DIFFERENCES BETWEEN THE NEW VARIETY 'YOGRAND RAPIDS' AND A SIMILAR VARIETY

| | 'Yograng Rapids' | 'Dazzling Yonew York' (U.S. Plant Pat. No. 17,438) |
|---|---|---|
| Flower color: | Light yellow with greyed red center | Golden yellow with dark orange center |
| Flower type: | Fully double decorative | Decorative with more open center |
| Growth habit: | More upright | More spreading |

Plant:

*Form, growth and habit.*—Herbaceous pot-type; compact but upright, strong and freely branching. Suitable for production-center budded or no bud removal.

*Plant height.*—22-25 cm.

*Plant height (inflorescence included).*—24-28 cm.

*Plant width.*—16-19 cm.

Roots:

*Number of days to initiate roots.*—4 days at about 22 degrees C.

*Number of days to produce a rooted cutting.*—10 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 137B.

*Lower surface.*—Closest to RHS 137C.

*Mature, leaf color, upper surface.*—Closest to RHS 137A.

*Lower surface.*—Closest to RHS 137C.

*Length.*—7.5-9.0 cm.

*Width.*—4.5-6.3 cm.

*Shape.*—Ovate.

*Base shape.*—Attenuate.

*Apex shape.*—Mucronulate to abuptly acute.

*Margin.*—Palmately lobed; serrated.

*Texture, upper surface.*—Bifid T-shaped hairs.

*Lower surface.*—Bifid T-shaped hairs.

*Color of veins, upper surface.*—Closest to RHS 144B.

*Color of veins, lower surface.*—Closest to RHS 144B.

*Petiole color.*—Closest to RHS 144B.

*Length.*—1.5-2.0 cm.

*Diameter.*—0.2 cm.

*Texture.*—Bifid T-shaped hairs.

Stem:

*Quantity of main branches per plant.*—3-4.

*Quantity of leaves per branch.*—8-10.

*Color of stem.*—RHS 146B.

*Length of stem.*—20-23 cm.

*Diameter.*—0.3-0.4 cm.

*Length of internodes.*—0.5-1.5 cm.

*Texture.*—Bifid T-shaped hairs.

*Color of peduncle.*—RHS 146B to RHS 146C.

*Length of peduncle.*—0.7-3.1 cm.

*Peduncle diameter.*—0.15 cm.

*Texture.*—Bifid T-shaped hairs.

Inflorescence:

*Type.*—Composite type, solitary inflorescences (decorative-type) borne terminally above foliage, ray florets arranged acropetally on a capitulum.

*Quantity of short days to flowering (response time).*—52-57 days grown with center bud removal.

*Quantity of inflorescences per plant.*—7-10.

*Lastingness of individual blooms on the plant.*—About 34 days.

*Fragrance.*—Slight.

Bud (just before opening/showing color):

*Color.*—RHS 181A.

*Length.*—1.5-1.7 cm.

*Width.*—0.5-0.7 cm.

*Shape.*—Oblate.

Immature inflorescence:

*Diameter.*—4.5-5.5 cm.

*Color of ray florets, upper surface.*—Between RHS 8A and RHS 9C.

*Lower surface.*—RHS 8C with overlay of RHS 182B and RHS 182C, heavier along the mid-vein.

Mature inflorescence:

*Diameter.*—6-7 cm.

*Total diameter of 'disc'.*—0.5 cm.

Ray florets:

*Average quantity of florets.*—Approximately 150.

*Color of florets, upper surface.*—RHS 8B to RHS 8C.

*Lower surface.*—RHS 8C with overlay of RHS 182B and RHS 182C, heavier along the mid-vein.

*Length.*—2.6-2.9 cm.

*Width.*—0.9-1.2 cm.

*Shape.*—Oblanceolate to oblong.

*Apex shape.*—Praemorse.

*Margin.*—Entire.

*Texture, upper surface.*—Papillose.

*Lower surface.*—Papillose.

Disc florets:

*Average quantity of florets.*—30-34.

*Color of florets.*—RHS 2C basally; RHS 1B at apex.

*Length.*—0.5-0.6 cm.

*Width.*—0.1 cm.

*Shape.*—Tubular, enlongated.

*Apex shape.*—Acute, 5 pointed.

Phyllaries:

*Quantity.*—15-20.

*Color, upper surface.*—RHS 137A, with margins becoming translucent and papery and about RHS 166B.

*Lower surface.*—Same.

*Length.*—0.5 cm.

*Width.*—0.3-0.4 cm.

*Shape.*—Lanceolate.

*Apex shape.*—Obtuse.

*Based.*—Fused.

*Margins.*—Entire.

*Texture, upper surface.*—Glossy and smooth.

*Lower surface.*—Bifid T-shaped hairs.

Reproductive organs:

*Pistil.*—1.

*Length.*—0.7-0.8 cm.

*Style color.*—RHS 1C.

*Style length.*—0.5 cm.

*Stigma color.*—RHS 1B.

*Stigma shape.*—Bi-parted.

*Ovary color.*—RHS 155C.

*Stamens.*—4.
*Color of filaments.*—RHS 1C.
*Length filaments.*—0.4 cm.
*Anther color.*—RHS 15C.
*Anther length.*—0.2 cm.
*Anther shape.*—Oblong.
*Color of pollen.*—RHS 15A.
*Pollen amount.*—Moderate.
*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yogrand Rapids,' substantially as illustrated and described herein.

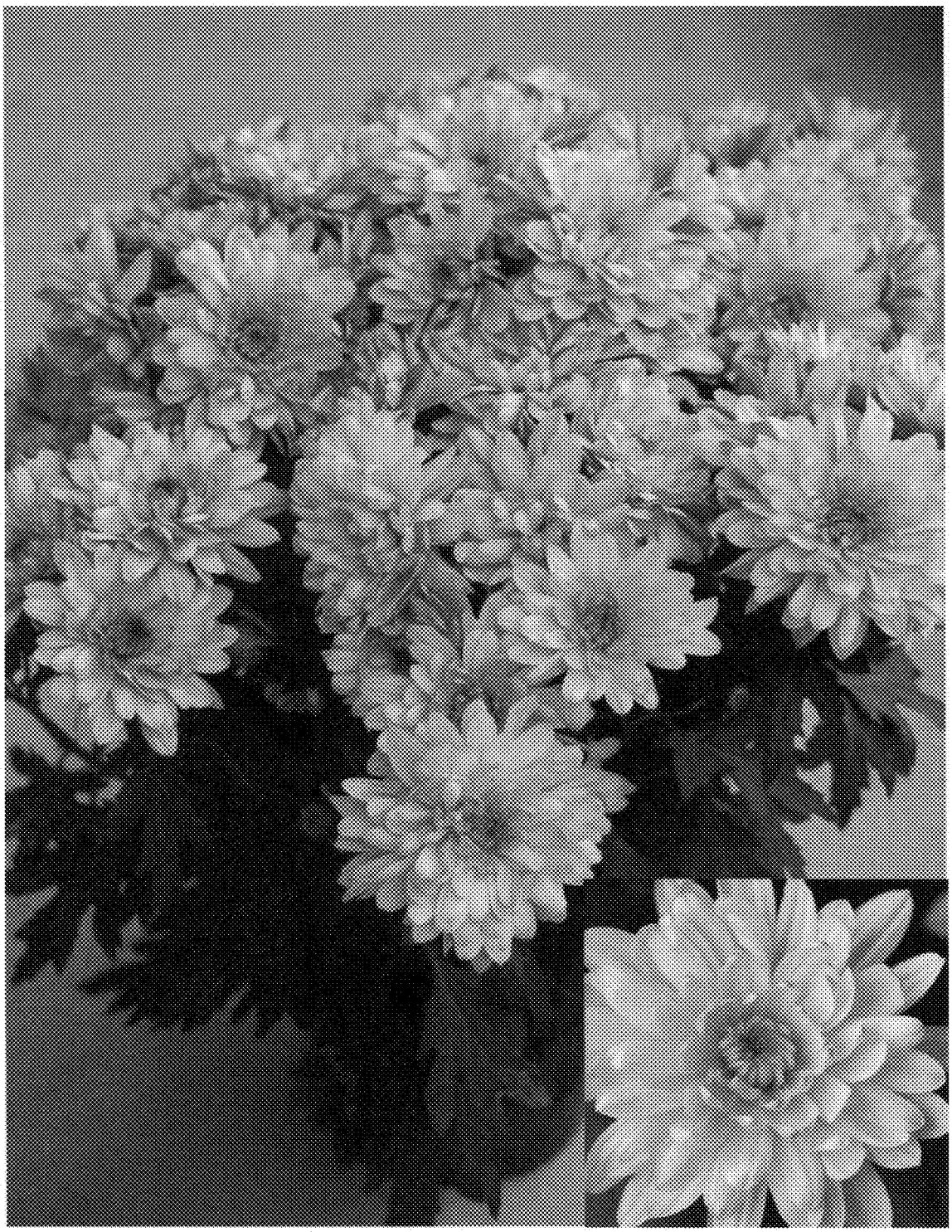

* * * * *